(12) United States Patent
Anderson et al.

(10) Patent No.: US 10,390,720 B2
(45) Date of Patent: *Aug. 27, 2019

(54) LEADLESS PACING SYSTEM INCLUDING SENSING EXTENSION

(71) Applicant: Medtronic, Inc., Minneapolis, MN (US)

(72) Inventors: Thomas A Anderson, New Hope, MN (US); Todd J Sheldon, North Oaks, MN (US); Matthew D Bonner, Plymouth, MN (US); Noelle C Neafus, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 485 days.

This patent is subject to a terminal disclaimer.

(21) Appl. No.: 14/694,952

(22) Filed: Apr. 23, 2015

(65) Prior Publication Data

US 2016/0015287 A1  Jan. 21, 2016

Related U.S. Application Data

(60) Provisional application No. 62/025,690, filed on Jul. 17, 2014.

(51) Int. Cl.
*A61B 5/04* (2006.01)
*A61B 5/042* (2006.01)
(Continued)

(52) U.S. Cl.
CPC .......... *A61B 5/0422* (2013.01); *A61B 5/0452* (2013.01); *A61B 5/686* (2013.01);
(Continued)

(58) Field of Classification Search
CPC ..... A61B 5/0422; A61B 5/0452; A61B 5/686; A61N 1/056; A61N 1/362; A61N 1/368; A61N 1/37205; A61N 1/3756
See application file for complete search history.

(56) References Cited

U.S. PATENT DOCUMENTS 3,486,506 A   12/1969   Auphan
3,659,615 A    5/1972   Enger
(Continued)

FOREIGN PATENT DOCUMENTS

CN   101185789 A   5/2008
CN   101284160 A   10/2008
(Continued)

OTHER PUBLICATIONS

US 8,116,861 B2, 02/2012, Root et al. (withdrawn)
(Continued)

*Primary Examiner* — Lindsey G Wehrheim

(57) ABSTRACT

A leadless pacing system includes a leadless pacing device and a sensing extension extending from a housing of the leadless pacing device. The sensing extension includes one or more electrodes with which the leadless pacing device may sense electrical cardiac activity. The one or more electrodes of the sensing extension may be carried by a self-supporting body that is configured to passively position the one or more electrodes proximate or within a chamber of the heart other than the chamber in which the LPD is implanted.

14 Claims, 8 Drawing Sheets

(51) Int. Cl.
  *A61B 5/00* (2006.01)
  *A61N 1/362* (2006.01)
  *A61B 5/0452* (2006.01)
  *A61N 1/375* (2006.01)
  *A61N 1/368* (2006.01)
  *A61N 1/372* (2006.01)
  *A61N 1/05* (2006.01)

(52) U.S. Cl.
  CPC ............ *A61N 1/362* (2013.01); *A61N 1/368* (2013.01); *A61N 1/3756* (2013.01); *A61N 1/37205* (2013.01); *A61N 1/056* (2013.01)

(56) References Cited

U.S. PATENT DOCUMENTS

| | | | |
|---|---|---|---|
| 3,693,625 | A | 9/1972 | Auphan |
| 3,835,864 | A | 9/1974 | Rasor et al. |
| 3,943,936 | A | 3/1976 | Rasor et al. |
| 4,157,720 | A | 6/1979 | Greatbatch |
| RE30,366 | E | 8/1980 | Rasor et al. |
| 4,256,115 | A | 3/1981 | Bilitch |
| 4,333,469 | A | 6/1982 | Jeffcoat et al. |
| 5,170,784 | A | 12/1992 | Ramon et al. |
| 5,193,540 | A | 3/1993 | Schulman et al. |
| 5,193,539 | A | 6/1993 | Schulman et al. |
| 5,243,977 | A | 9/1993 | Trabucco et al. |
| 5,312,439 | A | 5/1994 | Loeb |
| 5,324,316 | A | 6/1994 | Schulman et al. |
| 5,404,877 | A | 4/1995 | Nolan et al. |
| 5,405,367 | A | 4/1995 | Schulman et al. |
| 5,411,535 | A | 5/1995 | Fujii et al. |
| 5,441,527 | A | 8/1995 | Erickson et al. |
| 5,674,259 | A | 10/1997 | Gray |
| 5,792,208 | A | 8/1998 | Gray |
| 5,814,089 | A | 9/1998 | Stokes et al. |
| 5,843,132 | A | 12/1998 | Ilvento |
| 5,895,414 | A | 4/1999 | Sanchez-Zambrano |
| 5,954,757 | A | 9/1999 | Gray |
| 5,970,986 | A | 10/1999 | Bolz et al. |
| 5,987,352 | A | 11/1999 | Klein et al. |
| 6,044,300 | A | 3/2000 | Gray |
| 6,051,017 | A | 4/2000 | Loeb et al. |
| 6,141,588 | A | 10/2000 | Cox et al. |
| 6,144,879 | A | 11/2000 | Gray et al. |
| 6,175,764 | B1 | 1/2001 | Loeb et al. |
| 6,181,965 | B1 | 1/2001 | Loeb et al. |
| 6,185,452 | B1 | 2/2001 | Schulman et al. |
| 6,185,455 | B1 | 2/2001 | Loeb et al. |
| 6,208,894 | B1 | 3/2001 | Schulman et al. |
| 6,214,032 | B1 | 4/2001 | Loeb et al. |
| 6,240,316 | B1 | 5/2001 | Richmond et al. |
| 6,315,721 | B2 | 11/2001 | Schulman et al. |
| 6,415,184 | B1 | 7/2002 | Ishikawa et al. |
| 6,445,953 | B1 | 9/2002 | Bulkes et al. |
| 6,592,518 | B2 | 7/2003 | Denker et al. |
| 6,628,989 | B1 | 9/2003 | Penner et al. |
| 6,654,638 | B1 | 11/2003 | Sweeny |
| 6,733,485 | B1 | 5/2004 | Whitehurst et al. |
| 6,735,474 | B1 | 5/2004 | Loeb et al. |
| 6,735,475 | B1 | 5/2004 | Whitehurst et al. |
| 6,738,672 | B2 | 5/2004 | Schulman et al. |
| 6,764,446 | B2 | 7/2004 | Wolinsky et al. |
| 6,788,975 | B1 | 9/2004 | Whitehurst et al. |
| 6,804,561 | B2 | 10/2004 | Stover |
| 6,871,099 | B1 | 3/2005 | Whitehurst et al. |
| 6,907,285 | B2 | 6/2005 | Denker et al. |
| 6,917,833 | B2 | 7/2005 | Denker et al. |
| 6,941,171 | B2 | 9/2005 | Mann et al. |
| 6,947,782 | B2 | 9/2005 | Schulman et al. |
| 7,003,350 | B2 | 2/2006 | Denker et al. |
| 7,006,864 | B2 | 2/2006 | Echt et al. |
| 7,024,248 | B2 | 4/2006 | Penner et al. |
| 7,050,849 | B2 | 5/2006 | Echt et al. |
| 7,054,692 | B1 | 5/2006 | Whitehurst et al. |
| 7,082,336 | B2 | 7/2006 | Ransbury et al. |
| 7,103,408 | B2 | 9/2006 | Haller et al. |
| 7,114,502 | B2 | 10/2006 | Schulman et al. |
| 7,120,992 | B2 | 10/2006 | He et al. |
| 7,132,173 | B2 | 11/2006 | Daulton |
| 7,167,751 | B1 | 1/2007 | Whitehurst et al. |
| 7,177,698 | B2 | 2/2007 | Klosterman et al. |
| 7,184,830 | B2 | 2/2007 | Echt et al. |
| 7,198,603 | B2 | 4/2007 | Penner et al. |
| 7,200,437 | B1 | 4/2007 | Nabutovsky et al. |
| 7,203,548 | B2 | 4/2007 | Whitehurst et al. |
| 7,214,189 | B2 | 5/2007 | Zdeblick |
| 7,236,821 | B2 | 6/2007 | Cates et al. |
| 7,236,829 | B1 | 6/2007 | Farazi et al. |
| 7,260,436 | B2 | 8/2007 | Kilgore et al. |
| 7,283,874 | B2 | 10/2007 | Penner |
| 7,286,883 | B2 | 10/2007 | Schulman et al. |
| 7,292,890 | B2 | 11/2007 | Whitehurst et al. |
| 7,294,108 | B1 | 11/2007 | Bornzin et al. |
| 7,295,879 | B2 | 11/2007 | Denker et al. |
| 7,310,556 | B2 | 12/2007 | Bulkes |
| 7,330,756 | B2 | 2/2008 | Marnfeldt |
| 7,343,204 | B2 | 3/2008 | Schulman et al. |
| 7,351,921 | B1 | 4/2008 | Haller et al. |
| 7,363,082 | B2 | 4/2008 | Ransbury et al. |
| 7,428,438 | B2 | 9/2008 | Parramon et al. |
| 7,437,193 | B2 | 10/2008 | Parramon et al. |
| 7,444,180 | B2 | 10/2008 | Kuzma et al. |
| 7,450,998 | B2 | 11/2008 | Zilberman et al. |
| 7,493,172 | B2 | 2/2009 | Whitehurst et al. |
| 7,513,257 | B2 | 4/2009 | Schulman et al. |
| 7,519,421 | B2 | 4/2009 | Denker et al. |
| 7,519,424 | B2 | 4/2009 | Dennis et al. |
| 7,529,589 | B2 | 5/2009 | Williams et al. |
| 7,532,932 | B2 | 5/2009 | Denker et al. |
| 7,532,933 | B2 | 5/2009 | Hastings et al. |
| 7,535,296 | B2 | 5/2009 | Bulkes et al. |
| 7,555,345 | B2 | 6/2009 | Wahlstrand et al. |
| 7,558,631 | B2 | 7/2009 | Cowan et al. |
| 7,565,195 | B1 | 7/2009 | Kroll et al. |
| 7,587,241 | B2 | 9/2009 | Parramon et al. |
| 7,606,621 | B2 | 10/2009 | Brisken et al. |
| 7,610,092 | B2 | 10/2009 | Cowan et al. |
| 7,616,990 | B2 | 11/2009 | Chavan et al. |
| 7,616,992 | B2 | 11/2009 | Dennis et al. |
| 7,617,007 | B2 | 11/2009 | Williams et al. |
| 7,627,371 | B2 | 12/2009 | Wang et al. |
| 7,627,376 | B2 | 12/2009 | Dennis et al. |
| 7,627,383 | B2 | 12/2009 | Haller et al. |
| 7,630,767 | B1 | 12/2009 | Poore et al. |
| 7,634,313 | B1 | 12/2009 | Kroll et al. |
| 7,637,867 | B2 | 12/2009 | Zdeblick |
| 7,640,060 | B2 | 12/2009 | Zdeblick |
| 7,640,061 | B2 | 12/2009 | He et al. |
| 7,640,601 | B2 | 1/2010 | Lee |
| 7,647,109 | B2 | 1/2010 | Hastings et al. |
| 7,650,186 | B2 | 1/2010 | Hastings et al. |
| 7,706,892 | B2 | 4/2010 | Colvin et al. |
| 7,713,194 | B2 | 5/2010 | Zdeblick |
| 7,734,343 | B2 | 6/2010 | Ransbury et al. |
| 7,747,335 | B2 | 6/2010 | Williams |
| 7,751,881 | B2 | 7/2010 | Cowan et al. |
| 7,766,216 | B2 | 8/2010 | Daulton |
| 7,771,838 | B1 | 8/2010 | He et al. |
| 7,781,683 | B2 | 8/2010 | Haller et al. |
| 7,809,438 | B2 | 10/2010 | Echt et al. |
| 7,822,480 | B2 | 10/2010 | Park et al. |
| 7,826,903 | B2 | 11/2010 | Denker et al. |
| 7,840,282 | B2 | 11/2010 | Williams et al. |
| 7,848,815 | B2 | 12/2010 | Brisken et al. |
| 7,848,823 | B2 | 12/2010 | Drasler et al. |
| 7,860,564 | B2 | 12/2010 | Root et al. |
| 7,860,570 | B2 | 12/2010 | Whitehurst et al. |
| 7,890,173 | B2 | 2/2011 | Brisken et al. |
| 7,894,907 | B2 | 2/2011 | Cowan et al. |
| 7,899,541 | B2 | 3/2011 | Cowan et al. |
| 7,899,542 | B2 | 3/2011 | Cowan et al. |
| 7,899,554 | B2 | 3/2011 | Williams et al. |
| 7,904,167 | B2 | 3/2011 | Klosterman et al. |

(56) References Cited

U.S. PATENT DOCUMENTS

| | | |
|---|---|---|
| 7,930,031 B2 | 4/2011 | Penner |
| 7,937,148 B2 | 5/2011 | Jacobson |
| 7,945,333 B2 | 5/2011 | Jacobson |
| 7,954,533 B2 | 6/2011 | Nonaka et al. |
| 7,957,805 B2 | 6/2011 | He |
| 7,979,126 B2 | 7/2011 | Payne et al. |
| 7,991,467 B2 | 8/2011 | Markowitz et al. |
| 7,996,097 B2 | 8/2011 | DiBernardo et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,032,220 B2 | 10/2011 | Kuzma |
| 8,032,227 B2 | 10/2011 | Parramon et al. |
| 8,078,279 B2 | 12/2011 | Dennis et al. |
| 8,078,283 B2 | 12/2011 | Cowan et al. |
| 8,116,883 B2 | 2/2012 | Williams et al. |
| 8,126,561 B2 | 2/2012 | Chavan et al. |
| 8,127,424 B2 | 3/2012 | Haller et al. |
| 8,165,696 B2 | 4/2012 | McClure et al. |
| 8,185,212 B2 | 5/2012 | Carbunaru et al. |
| 8,204,595 B2 | 6/2012 | Pianca et al. |
| 8,224,449 B2 | 7/2012 | Carbunaru et al. |
| 8,239,045 B2 | 8/2012 | Ransbury et al. |
| 8,240,780 B1 | 8/2012 | Klimes |
| 8,295,939 B2 | 10/2012 | Jacobson |
| 8,301,242 B2 | 10/2012 | Root et al. |
| 8,301,262 B2 | 10/2012 | Mi et al. |
| 8,311,627 B2 | 11/2012 | Root et al. |
| 8,315,701 B2 | 11/2012 | Cowan et al. |
| 8,321,036 B2 | 11/2012 | Brockway et al. |
| 8,332,036 B2 | 12/2012 | Hastings et al. |
| 8,340,780 B2 | 12/2012 | Hastings et al. |
| 8,352,025 B2 | 1/2013 | Jacobson |
| 8,352,028 B2 | 1/2013 | Wenger |
| 8,359,098 B2 | 1/2013 | Lund et al. |
| 8,364,267 B2 | 1/2013 | Schleicher et al. |
| 8,364,276 B2 | 1/2013 | Willis |
| 8,364,278 B2 | 1/2013 | Pianca et al. |
| 8,364,280 B2 | 1/2013 | Marnfeldt et al. |
| 8,368,051 B2 | 2/2013 | Ting et al. |
| 8,374,696 B2 | 2/2013 | Sanchez et al. |
| 8,386,051 B2 | 2/2013 | Rys |
| 8,457,742 B2 | 6/2013 | Jacobson |
| 8,478,408 B2 | 7/2013 | Hastings et al. |
| 8,478,431 B2 | 7/2013 | Griswold et al. |
| 8,489,205 B2 | 7/2013 | Stotts et al. |
| 8,494,637 B2 | 7/2013 | Cowan et al. |
| 8,494,642 B2 | 7/2013 | Cowan et al. |
| 8,494,644 B2 | 7/2013 | Cowan et al. |
| 8,504,156 B2 | 8/2013 | Bonner et al. |
| 8,527,068 B2 | 9/2013 | Ostroff |
| 8,532,790 B2 | 9/2013 | Griswold |
| 8,541,131 B2 | 9/2013 | Lund et al. |
| 8,543,190 B2 | 9/2013 | Wasson et al. |
| 8,543,204 B2 | 9/2013 | Demmer et al. |
| 8,543,205 B2 | 9/2013 | Ostroff |
| 8,543,216 B2 | 9/2013 | Carbunaru et al. |
| 8,548,605 B2 | 10/2013 | Ollivier |
| 8,560,892 B2 | 10/2013 | Nicholes |
| 8,565,897 B2 | 10/2013 | Regnier et al. |
| 8,588,926 B2 | 11/2013 | Moore et al. |
| 8,615,310 B2 | 12/2013 | Khairkhahan et al. |
| 8,626,294 B2 | 1/2014 | Sheldon et al. |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,922 B2 | 2/2014 | Root et al. |
| 8,660,660 B2 | 2/2014 | Dai et al. |
| 8,670,842 B1 | 3/2014 | Bornzin et al. |
| 8,700,181 B2 | 4/2014 | Bornzin et al. |
| 2003/0114905 A1 | 6/2003 | Kuzma |
| 2004/0015204 A1 | 1/2004 | Whitehurst et al. |
| 2004/0073267 A1 | 4/2004 | Holzer |
| 2004/0093039 A1 | 5/2004 | Schumert |
| 2004/0122477 A1 | 6/2004 | Whitehurst et al. |
| 2004/0133242 A1 | 7/2004 | Chapman et al. |
| 2004/0147973 A1 | 7/2004 | Hauser |
| 2004/0162590 A1 | 8/2004 | Whitehurst et al. |
| 2004/0172089 A1 | 9/2004 | Whitehurst et al. |
| 2005/0055061 A1 | 3/2005 | Holzer |
| 2005/0070962 A1 | 3/2005 | Echt et al. |
| 2005/0256549 A1 | 11/2005 | Holzer |
| 2005/0288717 A1 | 12/2005 | Sunagawa |
| 2006/0074449 A1 | 4/2006 | Denker et al. |
| 2006/0135999 A1 | 6/2006 | Bodner et al. |
| 2006/0136005 A1 | 6/2006 | Brisken et al. |
| 2006/0173497 A1 | 8/2006 | Mech et al. |
| 2006/0241705 A1 | 10/2006 | Neumann et al. |
| 2006/0241732 A1 | 10/2006 | Denker et al. |
| 2007/0027508 A1 | 2/2007 | Cowan et al. |
| 2007/0060961 A1 | 3/2007 | Echt et al. |
| 2007/0073353 A1 | 3/2007 | Rooney et al. |
| 2007/0075905 A1 | 4/2007 | Denker et al. |
| 2007/0078490 A1 | 4/2007 | Cowan et al. |
| 2007/0088396 A1 | 4/2007 | Jacobson |
| 2007/0088397 A1 | 4/2007 | Jacobson |
| 2007/0106332 A1 | 5/2007 | Denker et al. |
| 2007/0106357 A1 | 5/2007 | Denker et al. |
| 2007/0118187 A1 | 5/2007 | Denker et al. |
| 2007/0129773 A1 | 6/2007 | Bulkes |
| 2007/0135883 A1 | 6/2007 | Drasler et al. |
| 2007/0150037 A1 | 6/2007 | Hastings et al. |
| 2007/0156204 A1 | 7/2007 | Denker et al. |
| 2007/0179550 A1 | 8/2007 | Dennis et al. |
| 2007/0179552 A1 | 8/2007 | Dennis et al. |
| 2007/0179581 A1 | 8/2007 | Dennis et al. |
| 2007/0185538 A1 | 8/2007 | Denker et al. |
| 2007/0210862 A1 | 9/2007 | Denker et al. |
| 2007/0219590 A1 | 9/2007 | Hastings et al. |
| 2007/0276444 A1 | 11/2007 | Gelbart et al. |
| 2007/0288076 A1 | 12/2007 | Bulkes et al. |
| 2007/0288077 A1 | 12/2007 | Bulkes et al. |
| 2007/0293904 A1 | 12/2007 | Gelbart et al. |
| 2007/0293908 A1 | 12/2007 | Cowan et al. |
| 2007/0293912 A1 | 12/2007 | Cowan et al. |
| 2007/0293913 A1 | 12/2007 | Cowan et al. |
| 2008/0033497 A1 | 2/2008 | Bulkes et al. |
| 2008/0039094 A1 | 2/2008 | Jeong et al. |
| 2008/0039904 A1 | 2/2008 | Bulkes et al. |
| 2008/0051854 A1 | 2/2008 | Bulkes et al. |
| 2008/0058886 A1 | 3/2008 | Williams |
| 2008/0077184 A1 | 3/2008 | Denker et al. |
| 2008/0077188 A1 | 3/2008 | Denker et al. |
| 2008/0097529 A1 | 4/2008 | Parramon et al. |
| 2008/0109054 A1 | 5/2008 | Hastings et al. |
| 2008/0119911 A1 | 5/2008 | Rosero |
| 2008/0132961 A1 | 6/2008 | Jaax et al. |
| 2008/0140154 A1 | 6/2008 | Loeb et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0319502 A1 | 12/2008 | Sunagawa et al. |
| 2009/0024180 A1 | 1/2009 | Kisker et al. |
| 2009/0048583 A1 | 2/2009 | Williams et al. |
| 2009/0082827 A1 | 3/2009 | Kveen et al. |
| 2009/0082828 A1 | 3/2009 | Ostroff |
| 2009/0171408 A1 | 7/2009 | Solem |
| 2009/0192570 A1 | 7/2009 | Jaax et al. |
| 2009/0198293 A1 | 8/2009 | Cauller et al. |
| 2009/0198295 A1 | 8/2009 | Dennis et al. |
| 2009/0198308 A1 | 8/2009 | Gross et al. |
| 2009/0326601 A1 | 12/2009 | Brisken et al. |
| 2010/0094367 A1 | 4/2010 | Sen |
| 2010/0137936 A1 | 6/2010 | Dennis et al. |
| 2010/0161002 A1 | 6/2010 | Aghassian et al. |
| 2010/0179628 A1 | 7/2010 | Towe et al. |
| 2010/0249883 A1 | 9/2010 | Zdeblick |
| 2010/0249885 A1 | 9/2010 | Colvin et al. |
| 2010/0286744 A1 | 11/2010 | Echt et al. |
| 2010/0304209 A1 | 12/2010 | Lund et al. |
| 2010/0305627 A1 | 12/2010 | Anderson |
| 2010/0305628 A1 | 12/2010 | Lund et al. |
| 2010/0305629 A1 | 12/2010 | Lund et al. |
| 2010/0312320 A1 | 12/2010 | Faltys et al. |

(56) References Cited

U.S. PATENT DOCUMENTS

| | | |
|---|---|---|
| 2011/0054555 A1 | 3/2011 | Williams et al. |
| 2011/0060392 A1 | 3/2011 | Zdeblick et al. |
| 2011/0071585 A1 | 3/2011 | Ransbury et al. |
| 2011/0071586 A1 | 3/2011 | Jacobson |
| 2011/0077708 A1 | 3/2011 | Ostroff |
| 2011/0077721 A1 | 3/2011 | Whitehurst et al. |
| 2011/0137378 A1 | 6/2011 | Klosterman et al. |
| 2011/0160801 A1 | 6/2011 | Markowitz et al. |
| 2011/0208260 A1 | 8/2011 | Jacobson |
| 2011/0245782 A1 | 10/2011 | Berthiaume et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0313490 A1 | 12/2011 | Parramon et al. |
| 2012/0059431 A1 | 3/2012 | Williams et al. |
| 2012/0081201 A1 | 4/2012 | Norgaard et al. |
| 2012/0095521 A1 | 4/2012 | Hintz |
| 2012/0095539 A1 | 4/2012 | Khairkhahan et al. |
| 2012/0109149 A1 | 5/2012 | Bonner et al. |
| 2012/0109236 A1 | 5/2012 | Jacobson et al. |
| 2012/0116489 A1 | 5/2012 | Khairkhahan et al. |
| 2012/0143271 A1 | 6/2012 | Root et al. |
| 2012/0158090 A1 | 6/2012 | Chavan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0179219 A1 | 7/2012 | Kisker et al. |
| 2012/0197352 A1 | 8/2012 | Carbunaru et al. |
| 2012/0197373 A1 | 8/2012 | Khairkhahan et al. |
| 2012/0232371 A1 | 9/2012 | Mech et al. |
| 2012/0290021 A1 | 11/2012 | Saurkar et al. |
| 2012/0290025 A1 | 11/2012 | Keimel |
| 2012/0316622 A1 | 12/2012 | Whitehurst et al. |
| 2012/0323099 A1 | 12/2012 | Mothilal et al. |
| 2013/0023975 A1 | 1/2013 | Locsin |
| 2013/0030483 A1 | 1/2013 | Demmer et al. |
| 2013/0035748 A1 | 2/2013 | Bonner et al. |
| 2013/0053921 A1* | 2/2013 | Bonner ............... A61N 1/3756 607/36 |
| 2013/0066169 A1 | 3/2013 | Rys et al. |
| 2013/0073004 A1 | 3/2013 | Root et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103109 A1 | 4/2013 | Jacobson |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1* | 5/2013 | Bornzin ............... A61N 1/3756 607/9 |
| 2013/0123872 A1 | 5/2013 | Bornzin et al. |
| 2013/0123875 A1 | 5/2013 | Varady et al. |
| 2013/0131159 A1 | 5/2013 | Ko et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0184790 A1 | 7/2013 | Schleicher et al. |
| 2013/0226259 A1 | 8/2013 | Penner et al. |
| 2013/0231710 A1 | 9/2013 | Jacobson |
| 2013/0234692 A1 | 9/2013 | Liang et al. |
| 2013/0235663 A1 | 9/2013 | Walsh et al. |
| 2013/0235672 A1 | 9/2013 | Walsh et al. |
| 2013/0238044 A1 | 9/2013 | Penner |
| 2013/0238056 A1 | 9/2013 | Poore et al. |
| 2013/0238072 A1 | 9/2013 | Deterre et al. |
| 2013/0238073 A1 | 9/2013 | Makdissi et al. |
| 2013/0238840 A1 | 9/2013 | Walsh et al. |
| 2013/0253309 A1 | 9/2013 | Allan et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijis et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0280270 A1 | 10/2013 | Sunday et al. |
| 2013/0282070 A1 | 10/2013 | Cowan et al. |
| 2013/0282073 A1 | 10/2013 | Cowan et al. |
| 2013/0302665 A1 | 11/2013 | Zhao et al. |
| 2013/0303872 A1 | 11/2013 | Taff et al. |
| 2013/0323099 A1 | 12/2013 | Li et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012342 A1 | 1/2014 | Penner et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0026016 A1 | 1/2014 | Nicholes |
| 2014/0031836 A1 | 1/2014 | Ollivier |
| 2014/0031837 A1 | 1/2014 | Perryman et al. |
| 2014/0039570 A1 | 2/2014 | Carroll et al. |
| 2014/0039578 A1 | 2/2014 | Whitehurst et al. |
| 2014/0039588 A1 | 2/2014 | Ok et al. |
| 2014/0039591 A1 | 2/2014 | Drasler et al. |
| 2014/0046395 A1 | 2/2014 | Regnier et al. |
| 2014/0058240 A1 | 2/2014 | Mothilal et al. |
| 2014/0072872 A1 | 3/2014 | Hodgkinson et al. |
| 2014/0100627 A1 | 4/2014 | Min |

FOREIGN PATENT DOCUMENTS

| | | |
|---|---|---|
| EP | 1541191 A1 | 6/2005 |
| EP | 2662113 A3 | 1/2014 |
| TW | I251986 B | 3/2006 |
| TW | I252007 B | 3/2006 |
| WO | 2006099425 A1 | 9/2006 |
| WO | 2009006531 A1 | 1/2009 |
| WO | 2009052480 A2 | 4/2009 |
| WO | 2012154599 A2 | 11/2012 |
| WO | 2013080038 A2 | 6/2013 |
| WO | 2012150000 | 11/2013 |
| WO | 20130184787 A1 | 12/2013 |
| WO | 2014046662 | 3/2014 |

OTHER PUBLICATIONS

Office Action from U.S. Appl. No. 14/694,910, dated Dec. 27, 2016, 8 pp.

Final Rejection from U.S. Appl. No. 14/694,910, dated Jun. 20, 2017, 9 pp.

Restriction Requirement from U.S. Appl. No. 14/694,910, dated Oct. 17, 2016, 8 pp.

Response to Restriction Requirement dated Oct. 17, 2016, from U.S. Appl. No. 14/694,910, filed Dec. 2, 2016, 2 pp.

Response to Office Action dated Dec. 27, 2016, from U.S. Appl. No. 14/694,910, filed Mar. 27, 2017, 12 pp.

Examiner's Answer from U.S. Appl. No. 14/694,910, dated Nov. 15, 2018, 9 pp.

Response to Final Office Action dated Jun. 20, 2017, from U.S. Appl. No. 14/694,910, filed Aug. 21, 2017, 8 pp.

Advisory Action from U.S. Appl. No. 14/694,910, dated Aug. 31, 2017, 3 pp.

Pre-Appeal Brief Request from U.S. Appl. No. 14/694,910, filed Sep. 20, 2017, 6 pp.

Notice of Appeal from U.S. Appl. No. 14/694,910, filed Sep. 20, 2017, 1 pp.

Reply Brief from co-pending U.S. Appl. No. 14/694,910, filed Jan. 15, 2019, 14 pp.

* cited by examiner

LEADLESS PACING SYSTEM INCLUDING SENSING EXTENSION

This application claims the benefit of U.S. Provisional Application Ser. No. 62/025,690 by Sheldon et al., filed Jul. 17, 2014, and entitled "LEADLESS PACING SYSTEM INCLUDING SENSING EXTENSION," which is incorporated herein by reference in its entirety.

TECHNICAL FIELD

The disclosure relates to cardiac pacing, and more particularly, to cardiac pacing using a leadless pacing device.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the proximal ends of the electrical leads are positioned at a target site. The pulse generator may provide electrical stimulation to the target site and/or monitor cardiac electrical activity at the target site via the electrodes.

A leadless pacing device has also been proposed for sensing electrical activity and/or delivering therapeutic electrical signals to the heart. The leadless pacing device may include one or more electrodes on its outer housing to deliver therapeutic electrical signals and/or sense intrinsic depolarizations of the heart. The leadless pacing device may be positioned within or outside of the heart and, in some examples, may be anchored to a wall of the heart via a fixation mechanism.

SUMMARY

The disclosure describes a leadless pacing system that includes a leadless pacing device (hereinafter, "LPD") and a sensing extension extending from a housing of the LPD, where the sensing extension includes one or more electrodes with which the LPD may sense electrical cardiac activity. The sensing extension is electrically coupled to a sensing module of the LPD via a conductive portion of the housing of the LPD. The one or more electrodes of the sensing extension may be carried by a self-supporting body that is configured to passively position the one or more electrodes proximate or within a chamber of the heart other than the chamber in which the LPD is implanted. In some examples, a proximal portion of the sensing extension is configured to reduce interference with the mechanical movement of the heart.

The sensing extension facilitates sensing, by the LPD, of electrical activity of a chamber of the heart other than the one in which the LPD is implanted. The LPD is configured to be implanted within a chamber of the heart of the patient and the sensing extension is configured to extend away from the LPD to position an electrode proximate or within another chamber of the heart, e.g., to sense electrical activity of the other chamber. In some examples, the sensing extension includes a feature configured to facilitate control of the sensing extension during implantation of the sensing extension in the patient. The feature may be, for example, an eyelet at a proximal end of the sensing extension, the eyelet being configured to receive a tether that may be used to control the positioning of the proximal end of the sensing extension during implantation of the leadless pacing system in a patient. The tether may also be used to confirm the LPD is fixed to the target tissue site, e.g., to perform a tug test.

In one aspect, the disclosure is directed to a system comprising a leadless pacing device comprising a stimulation module configured to generate pacing pulses, a sensing module, a processing module, a housing comprising a conductive portion, wherein the housing is configured to be implanted within a chamber of a heart of a patient and encloses the stimulation module, the sensing module, and the processing module, and a first electrode electrically coupled to the sensing module and the stimulation module. The system further comprises a sensing extension extending from the housing and comprising a self-supporting body extending from the housing and comprising a curved proximal portion, and a second electrode carried by the self-supporting body and electrically connected to the sensing module and the stimulation module via the conductive portion of the housing. The processing module is configured to control the sensing module to sense electrical cardiac activity via the second electrode.

In another aspect, the disclosure is directed to a method comprising controlling, by a processor, a stimulation module of a leadless pacing device to deliver a pacing pulse to a patient, the leadless pacing device comprising the stimulation module, a sensing module, the processor, a housing comprising a conductive portion, wherein the housing is configured to be implanted within a chamber of a heart of a patient and encloses the stimulation module, the sensing module, and the processor, and a first electrode electrically coupled to the sensing module and the stimulation module. The method further comprises controlling, by the processor, the sensing module of the leadless pacing device to sense electrical cardiac activity via the first electrode and a second electrode of a sensing extension that extends from the housing, the sensing extension further comprising a self-supporting body extending from the housing and comprising a curved proximal portion, and the second electrode carried by the self-supporting body and electrically connected to the sensing module and the stimulation module via the conductive portion of the housing.

In another aspect, the disclosure is directed to a system comprising a leadless pacing device comprising a stimulation module configured to generate pacing pulses, a sensing module, a processing module, a housing comprising a conductive portion, wherein the housing is configured to be implanted within a chamber of a heart of a patient and encloses the stimulation module, the sensing module, and the processing module, and wherein the conductive portion is electrically connected to the sensing module, and a first electrode electrically coupled to the sensing module and the stimulation module. The system further comprises a sensing extension extending from the housing and comprising a self-supporting body mechanically connected to the housing and comprising a conductor electrically connected to the conductive portion of the housing, a second electrode carried by the self-supporting body and electrically connected to the conductor, and an eyelet at a proximal end of the sensing extension.

In another aspect, the disclosure is directed to a system comprising a leadless pacing device comprising a stimulation module configured to generate pacing pulses, a sensing module, a processing module, a housing configured to be implanted within a chamber of a heart of a patient, wherein the housing encloses the stimulation module, the sensing module, and the processing module, and a first electrode electrically coupled to the sensing module and the stimulation module. The system further comprises an extension extending from the housing and comprising a body mechanically connected to the housing and comprising a conductor electrically connected to at least one of the sensing module or the stimulation module, a second electrode carried by the body and electrically connected to the conductor, and an eyelet at a proximal end of the extension.

In another aspect, the disclosure is directed to a method comprising controlling, by a processor, a stimulation module of a leadless pacing device to deliver a pacing pulse to a patient, the leadless pacing device comprising the stimulation module, a sensing module, the processor, a housing configured to be implanted within a chamber of a heart of a patient, wherein the housing encloses the stimulation module, the sensing module, and the processing module, and a first electrode electrically coupled to the sensing module and the stimulation module. The method further comprises controlling, by the processor, the sensing module of the leadless pacing device to sense electrical cardiac activity via the first electrode and a second electrode of a sensing extension that extends from the housing, the sensing extension further comprising a body mechanically connected to the housing and comprising a conductor electrically connected to the sensing module, a second electrode carried by the body and electrically connected to the conductor, and an eyelet at a proximal end of the extension.

In another aspect, the disclosure is directed to a computer-readable storage medium comprising computer-readable instructions for execution by a processor. The instructions cause a programmable processor to perform any whole or part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium is an article of manufacture and is non-transitory.

The details of one or more examples are set forth in the accompanying drawings and the description below. Other features, objects, and advantages will be apparent from the description and drawings, and from the claims.

DETAILED DESCRIPTION

Figure 1:
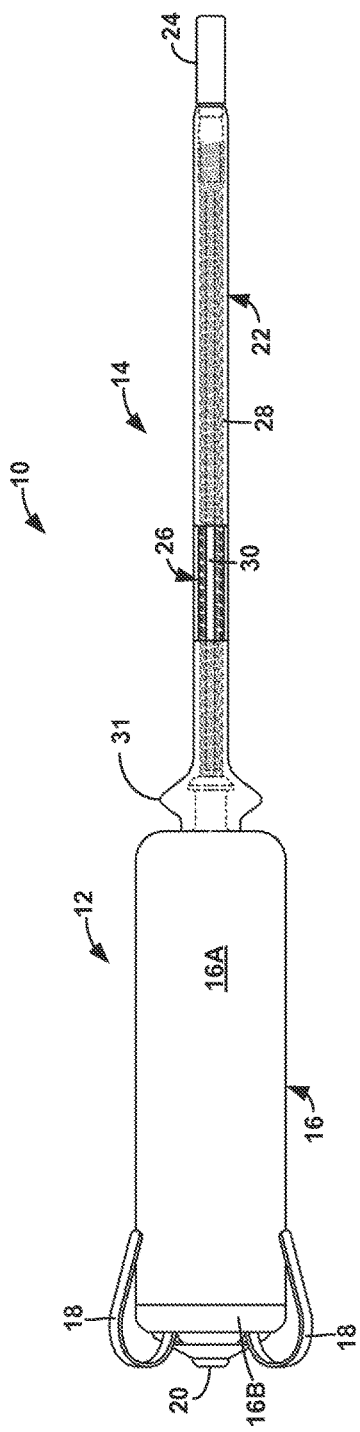
FIG. 1 illustrates an example leadless pacing system that comprises a leadless pacing device and a sensing extension.

A leadless pacing system includes an LPD and a sensing extension that is coupled to the LPD and configured to facilitate sensing of electrical activity of a chamber of the heart other than the one in which the LPD is implanted. The sensing extension includes one or more electrodes and a self-supporting body that extends away from an outer housing of the LPD. In contrast to leaded pacing systems, the leadless pacing systems described herein do not include leads that pass out of the heart. Rather, both the LPD and sensing extension are configured to be entirely implanted in a heart of a patient. In some examples, the sensing extension is sized to be entirely implanted within the same chamber of the heart as the LPD. In other examples, the LPD is configured to be implanted in a first chamber of the heart, and the sensing extension is sized to extend into another chamber.

The LPD is configured to be implanted within a first chamber (e.g., a ventricle) of a heart of a patient, and the sensing extension is configured to position one or more electrodes proximate or within a second chamber of the heart, e.g., to sense electrical activity of the second chamber. The sensing extension has a length sufficient to locate one or more electrodes of the sensing extension closer to the second chamber than any electrodes of the LPD. For example, the sensing extension may have a length selected to position the one or more electrodes of the sensing extension adjacent the right atrium or in the right atrium when the LPD is implanted in or near the apex of the right ventricle. The one or more electrodes of the sensing extension may be used to sense intrinsic ventricular electrical activity, as well as detect atrial electrical activity.

In some examples described herein, the self-supporting body is configured to passively (i.e., without any active fixation elements, such as tines or a fixation helix) position an electrode extension at a location away from the LPD, e.g., at a location proximate the second chamber of the heart. The self-supporting body may be flexible enough to reduce irritation to the tissue of the heart when the body contacts the tissue, but have sufficient rigidity to permit the sensing extension to extend away from the LPD housing and towards the second chamber, even in the presence of blood in the first chamber of the heart. The stiffness of the self-supporting body is selected to help prevent the body from collapsing in on itself and/or towards the LPD, e.g., in the presence of blood flow. In addition, the stiffness of the self-supporting body may be selected so that the body is configured to support its own weight, e.g., in the presence of gravity.

The sensing extension also includes a proximal portion that is configured to help reduce interference with the mechanical movement of the heart. For example, in examples in which the LPD is configured to be implanted within a ventricle of the heart and the sensing extension is configured to extend towards an atrium, the proximal portion of the sensing extension may be shaped and sized to reduce interference with the opening and closing of an atrioventricular valve (e.g., the tricuspid valve or the mitral valve). In addition, the proximal end of the sensing extension is configured to be atraumatic (e.g., blunt) in order to reduce irritation to the heart tissue if the proximal end comes into contact with the heart tissue. As an example of a configuration of a proximal portion that may help reduce interference with the mechanical movement of the heart, the proximal portion may be curved with one or more bends. For example, the proximal portion may define an L-shaped curve, a C-shaped curve, a pigtail, or any other suitable curve.

In some examples, a sensing extension also includes a feature configured to facilitate control of the sensing extension during implantation of the sensing extension in the heart. In these examples, the sensing extension may or may not have a self-supporting body. In some examples, the feature includes an eyelet at a proximal end of the sensing extension. A tether may be fed through the eyelet prior to introducing the LPD and the sensing extension in a heart of a patient. During the implantation process, a clinician may pull back on the tether to help control the position of the proximal end of the sensing extension, to confirm that the LPD is adequately fixed to the target tissue site (e.g., a "tug test" that confirms the LPD does not move in response to a pull on the tether). After implantation, the tether may be removed from the eyelet.

FIG. 1 is a conceptual illustration of an example leadless pacing system 10 that includes LPD 12 and sensing extension 14. LPD 12 is configured to be implanted within a chamber of a heart of a patient, e.g., to monitor electrical activity of the heart and/or provide electrical therapy to the heart. In the example shown in FIG. 1, LPD 12 includes outer housing 16, a plurality of fixation tines 18, and electrode 20. Sensing extension 14 includes self-supporting body 22, electrode 24, and conductor 26.

Outer housing 16 has a size and form factor that allows LPD 12 to be entirely implanted within a chamber of a heart of a patient. In some examples, outer housing 16 may have a cylindrical (e.g., pill-shaped) form factor. LPD 12 may include a fixation mechanism configured to fix LPD 12 to cardiac tissue. For example, in the example shown in FIG. 1, LPD 12 includes fixation tines 18 extending from housing 16 and configured to engage with cardiac tissue to substantially fix a position of housing 16 within the chamber of the heart. Fixation tines 18 are configured to anchor housing 16 to the cardiac tissue such that LPD 12 moves along with the cardiac tissue during cardiac contractions. Fixation tines 18 may be fabricated from any suitable material, such as a shape memory material (e.g., Nitinol). Although LPD 12 includes a plurality of fixation tines 18 that are configured to anchor LPD 12 to cardiac tissue in a chamber of a heart, in other examples, LPD 12 may be fixed to cardiac tissue using other types of fixation mechanisms, such as, but not limited to, barbs, coils, and the like.

Housing 16 houses electronic components of LPD 12, e.g., a sensing module for sensing cardiac electrical activity via electrodes 20, 24, and an electrical stimulation module for delivering electrical stimulation therapy via electrodes 20, 24. Electronic components may include any discrete and/or integrated electronic circuit components that implement analog and/or digital circuits capable of producing the functions attributed to LPD 12 described herein. In some examples, housing 16 may also house components for sensing other physiological parameters, such as acceleration, pressure, sound, and/or impedance.

Additionally, housing 16 may also house a memory that includes instructions that, when executed by one or more processors housed within housing 16, cause LPD 12 to perform various functions attributed to LPD 12 herein. In some examples, housing 16 may house a communication module that enables LPD 12 to communicate with other electronic devices, such as a medical device programmer. In some examples, housing 16 may house an antenna for wireless communication. Housing 16 may also house a power source, such as a battery. Housing 16 can be hermetically or near-hermetically sealed in order to help prevent fluid ingress into housing 16.

LPD 12 is configured to sense electrical activity of the heart and deliver electrical stimulation to the heart via electrodes 20, 24. LPD 12 comprises electrode 20 and sensing extension 14 comprises electrode 24. For example, electrode 20 may be mechanically connected to housing 16. As another example, electrode 20 may be defined by an outer portion of housing 16 that is electrically conductive. Fixation tines 18 may be configured to anchor LPD 12 to cardiac tissue such that electrode 20 maintains contact with the cardiac tissue.

Sensing extension 14 is configured to position electrode 24 proximate to or outside the chamber in which LPD 12 is implanted. For example, sensing extension 14 may be configured to position electrode 24 within a chamber other than the one in which LPD 12 resides. In this way, sensing extension 24 may extend the sensing capabilities of system 10. In the example shown in FIG. 1, electrode 24 is carried by self-supporting body 22 of sensing extension 14, and is located at a proximal end of body 22. In other examples, however, electrode 24 may have another position relative to body 22, such mid-way between housing 16 and the proximal end of body 22, or otherwise away from the proximal end of body 22. Electrode 24 may have any suitable configuration. For example, electrode 24 may have a ring-shaped configuration, or a partial-ring configuration. Electrode 24 may be formed from any suitable material, such as a titanium nitride coated metal.

In other examples, system 10 may include more than two electrodes. For example, LPD 12 and/or sensing extension 14 may have more than one electrode. As an example, one or more additional electrodes having the same polarity as electrode 24 may be carried by sensing extension 14. The one or more additional electrodes may be electrically connected to the same or a different electrical conductor than sensing extension 14. The additional electrodes of sensing extension 14 may increase the probability that an electrode of system 10 is positioned to sense electrical activity of a chamber of the heart other than the one in which LPD 12 is implanted.

In the example shown in FIG. 1, electrode 24 is electrically connected to at least some electronics of LPD 12 (e.g., a sensing module and a stimulation module) via electrical conductor 26 of sensing extension 14 and electrically conductive portion 16A of housing 16. Electrical conductor 26 is electrically connected to and extends between conductive portion 16A of housing 16 and electrode 24. Conductive portion 16A is electrically isolated from electrode 20, but is electrically connected to electrode 24, such that conductive portion 16A and electrode 24 have the same polarity and are electrically common. For example, electrode 20 may be carried by second portion 16B of housing 16, which is electrically isolated from conductive portion 16A. Conductive portion 16A of housing 16 is electrically connected to at least some electronics of LPD 12 (e.g., a sensing module, an electrical stimulation module, or both), such that conductive portion 16A defines part of an electrically conductive pathway from electrode 24 to the electronics. In some examples, conductive portion 16A may define at least a part of a power source case of LPD 12. The power source case may house a power source (e.g., a battery) of LPD 12.

In some examples, conductive portion 16A is substantially completely electrically insulated (e.g., completely electrically insulated or nearly completely electrically insulated. Substantially completely electrically insulating conductive portion 16A may help a sensing module of LPD 12 sense electrical cardiac activity with electrode 24 of sensing extension 14. For example, in examples in which LPD 12 and sensing extension are implanted in a right ventricle, as shown and described with respect to FIG. 3, substantially completely electrically insulating conductive portion 16A may help electrode 24 pick-up a stronger far field P-wave. In other examples, however, at least a part of conductive portion 16A may be exposed to define one or more electrodes, which have the same polarity as electrode 24.

Figure 2:
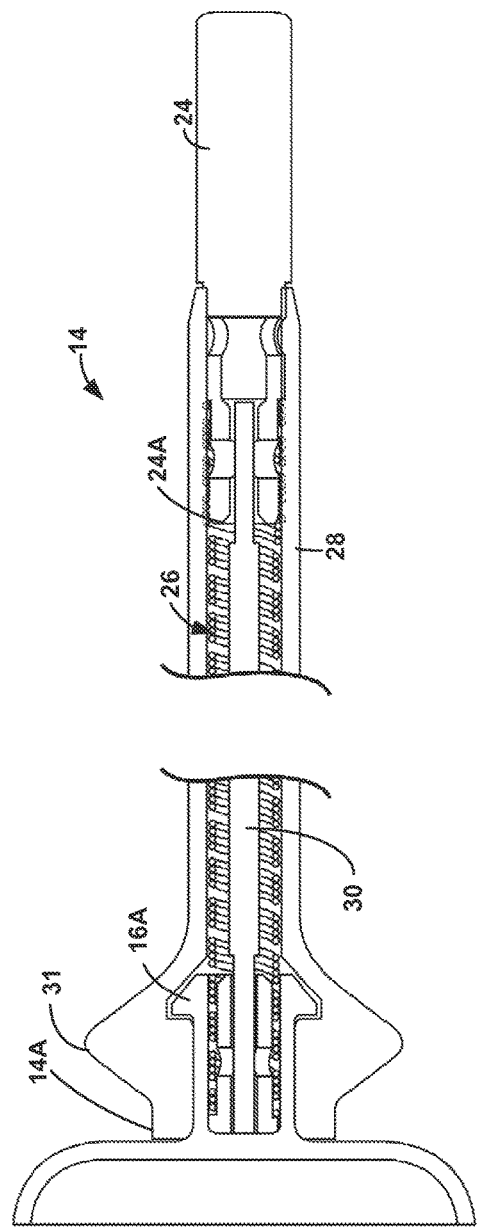
FIG. 2 is a schematic cross-sectional view of the sensing extension of FIG. 1.

As shown in FIG. 2, which is a schematic cross-sectional view of sensing extension 14 and a part of that conductive portion 16A of housing 16, in some examples, conductor 26 may be coiled around conductive portion 16A to establish an electrical connection between conductor 26 and conductive portion 16A. In other examples, however, an electrical connection between conductor 26 and conductive portion 16A may be established using another configuration. For example, conductor 26 may not be coiled within sensing extension 14 and may be crimped or otherwise placed in contact with conductive portion 16A near distal end 14A of sensing extension 14.

FIG. 2 also illustrates an example electrical connection between electrode 24 and conductor 26. In particular, FIG. 2 illustrates an example in which a proximal portion of conductor 26 is welded to a distal portion of electrode 24, the distal portion including distal end 24A. In other examples, electrode 24 and conductor 26 may be electrically connected using another configuration. As shown in FIG. 2, electrode 24 may be substantially closed at a proximal end in some examples, which may help prevent fluids from entering an inner portion (e.g., where conductor 26 is positioned) of sensing extension 14.

In the example shown in FIGS. 1 and 2, self-supporting body 22 of sensing extension 14 extends between housing 16 and electrode 24. Self-supporting body 22 has a stiffness that permits body 22 to substantially maintain (e.g., completely maintain or nearly maintain) its position relative to LPD 12, or at least the position of electrode 24 relative to LPD 12, even in the presence of gravity and in the presence of blood flow in the heart. For example, self-supporting body 22 may have a bending stiffness of about 0.8 $e^{-6}$ N-m$^2$ to about 4.8 $e^{-6}$ N-m$^2$ (about 0.8×10$^{-6}$ to about 4.8×10$^{-6}$ N-m$^2$), such as about 1.6 Newtons-square meter (N-m$^2$). In other examples, self-supporting bodies having other bending stiffness values may also be used.

Self-supporting body 22 is configured to passively position electrode 24 at a location away from LPD 12, e.g., proximate or within a chamber of the heart other than the one in which LPD 12 is implanted. For example, self-supporting body 22 may have sufficient rigidity (e.g., stiffness) to permit sensing extension 14 to extend away from housing 16, even as the sensing extension moves within blood in the chamber of the heart. In addition, self-supporting body 22 may be flexible enough to minimize irritation to the tissue of the heart, should body 22 contact the tissue.

In some examples, a bending stiffness of self-supporting body is substantially the same throughout the length of self-supporting body 22 (e.g., the same or nearly from a distal end to a proximal end of body 22). In other examples, self-supporting body 22 may have a variable stiffness along its length. For example, self-supporting body may decrease in stiffness from a distal end (closest to housing 16 LPD 12) to a proximal end, such that a distal portion of body 22 closest to housing 16 may have a higher stiffness than a proximal portion of body 22 closest to electrode 24 and including the proximal end. For example, the distal portion may be configured to have the highest stiffness and the proximal portion may be configured to have the lowest stiffness. A lower stiffness at the proximal portion of body 22 may help further minimize irritation to the tissue of the heart, should the proximal end of body 22 contact tissue, while the stiffer distal portion may permit body 22 to position electrode 24 at a location away from LPD 12.

In the example shown in FIGS. 1 and 2, electrical conductor 26 is covered by an electrically conductive material, such as a polymer (e.g., polyurethane) or silicone. For example, conductor 26 may be housed within a polyurethane or silicone sleeve 28, as shown in FIGS. 1 and 2. In some cases, coiled conductor 26 may not provide sufficient stiffness to sensing extension 14 to enable self-supporting body 22 to substantially maintain its position relative to LPD 12 in the presence of blood flow in the heart. Thus, in some examples, sensing extension 14 may also include a stiffness member 30, which has a higher stiffness than coiled conductor 26 (when coiled). In the example shown in FIGS. 1 and 2, self-supporting body 22 of sensing extension 14 is defined by conductor 26, sleeve 28, and stiffness member 30.

Stiffness member 30 has a stiffness that helps prevent self-supporting body 22 from collapsing in on itself and/or towards LPD 12, e.g., in the presence of blood flow. For example, in examples in which conductor 26 is coiled and is enclosed in a polyurethane or silicone sleeve, stiffness member 30 may have a stiffness that results in self-supporting body 22 having a stiffness of about 0.8 $e^{-6}$ N-m$^2$ to about 4.8 $e^{-6}$ N-m$^2$ (about 0.8×10$^{-6}$ to about 4.8×10$^{-6}$ N-m$^2$). The stiffness, however, for stiffness member 30 that may be suitable for providing the desired stiffness characteristics to self-supporting body 22 may depend on various factors, such as length of self-supporting body 22 and the diameter (or other cross-sectional dimensions in examples in which self-supporting body 22 has a non-circular cross-sectional shape when the cross-section is taken substantially perpendicular to a longitudinal axis) of self-supporting body 22. Stiffness member 30 may be more stiff as the length of self-supporting body 22 increases, and as the diameter of self-supporting body increases. A bigger diameter may cause the blood flow to push self-supporting body 22 around more within the heart. As with self-supporting body 22, in some examples, stiffness member 30 may also have a variable stiffness along its length or may have substantially the same stiffness along its length.

Stiffness member 30 may be formed from any suitable material non-metallic or metallic material, such as a nickel-cobalt-chromium-molybdenum alloy (e.g., MP35N, such as a 7×7 MP35N cable).

In addition, stiffness member 30 may limit the amount sensing extension 14 stretches in response to a pulling force applied to the proximal end of sensing extension 14 (the end furthest from LPD 12) during a tug test performed to confirm that LPD 12 is secured to a target tissue site, e.g., that tines 18 are securely engaged with tissue of the heart of the patient. In some examples, such as examples in which conductor 26 is coiled, conductor 26 may stretch (e.g., elongate) in response to the pulling force. However, stiffness member 30 may be configured to stretch less than conductor 26 in some examples, and, as a result, when a clinician applies a pulling force to the proximal end of sensing extension 14 (the end furthest from LPD 12) during a tug test to confirm that LPD 12 is secured to a target tissue site, stiffness member 30 may limit the amount sensing extension 14 stretches in response to the pulling relative to examples in which sensing extension 14 does not include stiffness member 30.

As shown in FIGS. 1 and 2, in some examples, stiffness member 30 extends through a center of coiled conductor 26 (e.g., conductor 26 may be coiled around member 30) and is coaxial with a longitudinal axis of sensing extension 14. In other examples however, stiffness member 30 may have another position within sensing extension 14.

In other examples, such as examples in which conductor 26 is not coiled, sensing extension 14 may not include stiffness member 30. For example, the material of sleeve 28, in combination with the conductor 26, may provide body 22 with sufficient stiffness to permit body 22 to maintain its position relative to LPD 12, even in the presence of gravity and in the presence of blood flow in the heart.

In some examples, in addition to, or instead of, electrically connecting electrode 24 to electronics of LPD 12 via electrical conductor 26, stiffening member 30 may be electrically conductive and may electrically connect electrode 24 to electronics of LPD 12. For example, a proximal portion of stiffening member 30 may be welded or otherwise electrically connected to a distal portion of electrode 24. Thus, in some examples, sensing extension 14 does not include electrical conductor 26 and stiffening member 30 may both electrically connect electrode 24 to electronics of LPD 12 and increases the stiffness of sensing extension 14, e.g., to help prevent self-supporting body 22 from collapsing in on itself and/or towards LPD 12. Stiffness member 30 may have a higher stiffness than, for example, sleeve 28. In examples in which both electrical conductor 26 and stiffening member 30 electrically connect electrode 24 to electronics of LPD 12, sensing extension 14 may provide redundant electrical pathways for electrically connecting electrode 24 to electronics of LPD 12.

In the example shown in FIGS. 1 and 2, system 10 includes retrieval member 31, which is positioned at or near the distal end of sensing extension 14, which is mechanically connected to outer housing 16 of LPD 12. Retrieval member 31 can be, for example, a bump, protrusion, or any other suitable feature that can be used to grasp system 10, e.g., when removing or implanting system 10 in a patient. For example, retrieval member 31 can be a bump configured to be grabbed by a snare. In some examples, retrieval member 31 is incorporated in a molded part used for insulating sensing extension 14, or may be formed integrally with outer housing 16. In other examples, retrieval member 31 can be separate from and attached to sensing extension 14, outer housing 16, or both.

Figure 3:
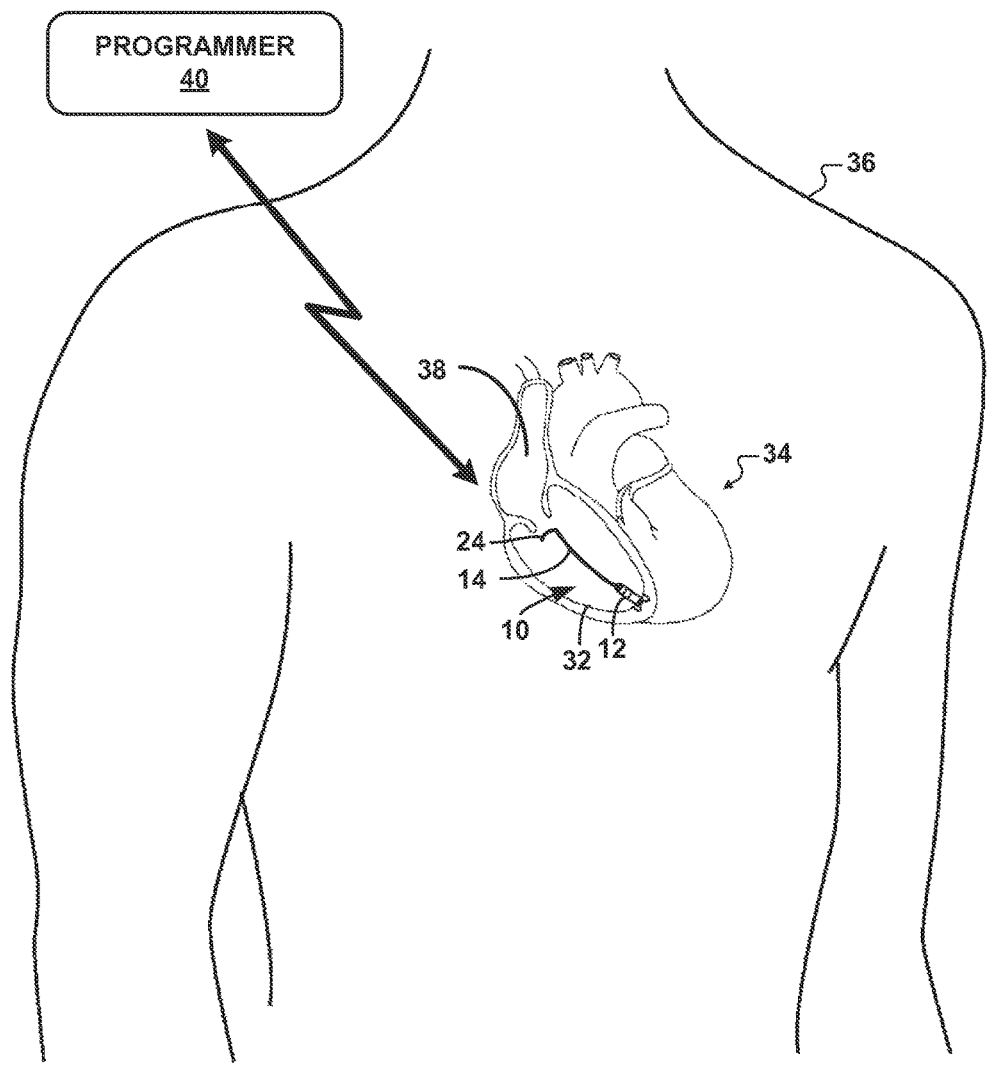
FIG. 3 is a conceptual illustration of the leadless pacing system of FIG. 1 implanted in a patient.

As discussed above, sensing extension 14 is configured to position electrode 24 proximate to or within a chamber of a heart other than the one in which LPD 12 is implanted. FIG. 3 illustrates system 10 implanted in right ventricle 32 of heart 34 of patient 36. In the example shown in FIG. 3, sensing extension 14 is configured to extend away from LPD 12 and towards right atrium 38 when LPD 12 is implanted in an apex of right ventricle 32. In some examples, sensing extension 14 may have a length that permits sensing extension 14 to remain in right ventricle 32 with LPD 12, as shown in FIG. 3. For example, sensing extension 14 may have a length of about 40 millimeters (mm) to about 150 mm, such as about 60 millimeters (as measured from the distal end connected to LPD 12 and a proximal end of electrode 24). A single chamber system 10 may provide the advantages of sensing electrical activity of two chambers (e.g., right ventricle 32 and right atrium 38 in the example shown in FIG. 3) without the burden of placing extension 14 in right atrium 38.

In examples in which extension 14 remains in the same chamber as LPD 12, a proximal portion of sensing extension 14 may be configured to help reduce interference with the mechanical movement of the heart, such as, in the example shown in FIG. 3, movement of the tricuspid valve. For example, electrode 24 at the proximal end of extension 14 may define an L-shaped curve, a C-shaped curve, a pigtail, or any other suitable curve, as shown with respect to electrodes 25A, 25B, and 25C in FIGS. 4A, 4B, and 4C, respectively. The L-shaped curve is also shown in FIG. 3.

Figure 4A:
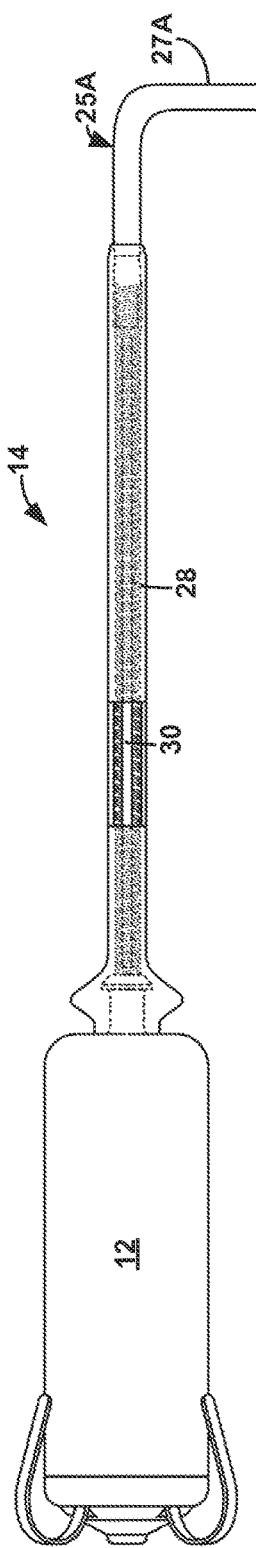
FIGS. 4A-4C illustrate example shapes of a proximal end of a sensing extension.
Figure 4B:
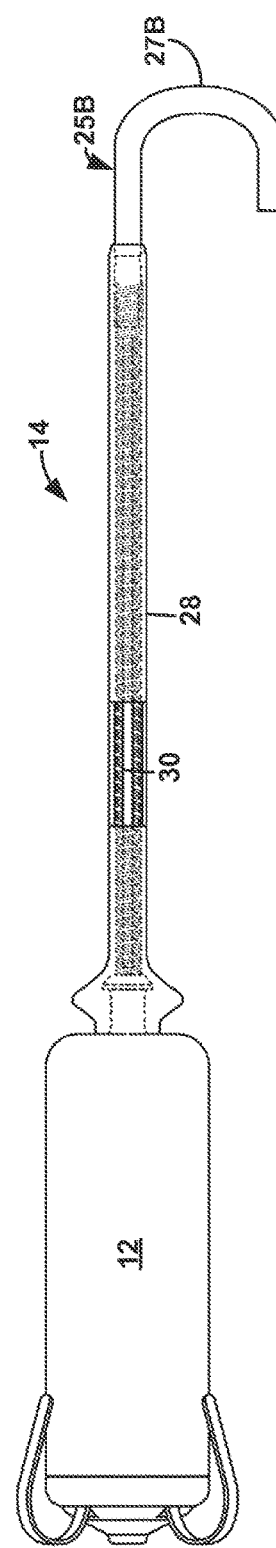
Figure 4C:
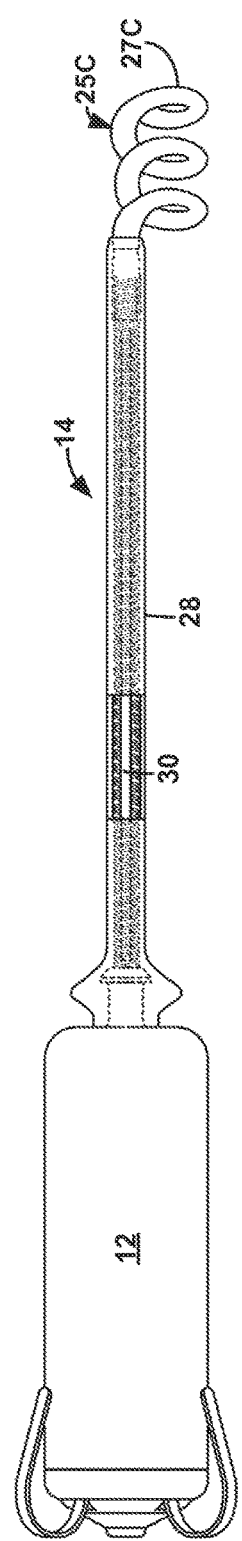

The L-shaped curve, the C-shaped curve, and the pigtail shaped curve shown in FIGS. 4A, 4B, and 4C may define curved or relatively flat surfaces (e.g., surfaces 27A-27C) against which the tricuspid valve (or other valve in the case of other implantation sites for LPD 12) may still substantially close, which may help prevent blood from back flowing into another chamber of heart 34, e.g., right atrium 38. In some examples, the shape of proximal portion of sensing extension 14 may be selected based on the implant location for system 10. Different shapes may help reduce interference with different valves and different implantation sites for LPD 12 and sensing extension 14.

In other examples, a portion of sensing extension 14 in addition to, or other than, electrode 24 may define the shapes shown in FIGS. 4A-4C. For example, sleeve 28 and stiffness member 30 may be configured to define the proximal portion shapes shown in FIGS. 4A-4C and electrode 24 may be positioned on an outer surface of sleeve 28.

In other examples, sensing extension 14 may have a length that enables at least electrode 24 to extend into right atrium 38 when LPD 12 is implanted in an apex of right ventricle 32. In examples in which sensing extension 14 extends into right atrium 38, sensing extension 14 may be relatively small and flexible enough to permit the tricuspid valve to sufficiently close around the sensing extension 14 to prevent backflow into right atrium 38 from right ventricle 32. For example, sensing extension 14 may be about 4 French (i.e., about 1.33 millimeters in diameter.

LPD 12 may sense electrical activity of right atrium 38 or right ventricle 32 with electrodes 20, 24. As shown in FIG. 3 sensing extension 14 is passive and extends away from LPD 12, which enables electrode 24 to be positioned relatively close to right atrium 38. The distance between electrode 24 and right atrium 38 may be less than the distance between electrode 20 of LPD 12 and right atrium 38. As a result, electrode 24 may be positioned to pick up higher amplitude P-waves than electrode 20. In this way, sensing extension 14 may facilitate atrial sensing when LPD 12 is implanted in right ventricle 32.

Rather than being affixed to cardiac tissue such that electrode 24 is in direct contact with heart 34, a proximal portion of sensing extension 14 is passive, such that sensing extension 14 may move within right ventricle 32. However, due at least in part to the self-supporting configuration of body 22 (FIGS. 1 and 2), sensing extension 14 is configured to continue to extend away from LPD 12 and towards right atrium 38, even in the presence of blood flow from right atrium 38 to right ventricle 32. Providing self-supporting member 22 of sensing extension 14 with some flexibility may enable sensing extension 14 to minimize interference with blood flow in right ventricle 32 (or another chamber if LPD 12 is implanted in another chamber).

Also shown in FIG. 3 is medical device programmer 40, which is configured to program LPD 12 and retrieve data from LPD 12. Programmer 40 may be a handheld computing device, desktop computing device, a networked computing device, etc. Programmer 40 may include a computer-readable storage medium having instructions that cause a processor of programmer 40 to provide the functions attributed to programmer 40 in the present disclosure. LPD 12 may wirelessly communicate with programmer 40. For example, LPD 12 may transfer data to programmer 40 and may receive data from programmer 40. Programmer 40 may also wirelessly program and/or wirelessly charge LPD 12.

Data retrieved from LPD 12 using programmer 40 may include cardiac EGMs stored by LPD 12 that indicate electrical activity of heart 34 and marker channel data that indicates the occurrence and timing of sensing, diagnosis, and therapy events associated with LPD 12. Data transferred to LPD 12 using programmer 40 may include, for example, operational programs for LPD 12 that causes LPD 12 to operate as described herein.

Figure 5:
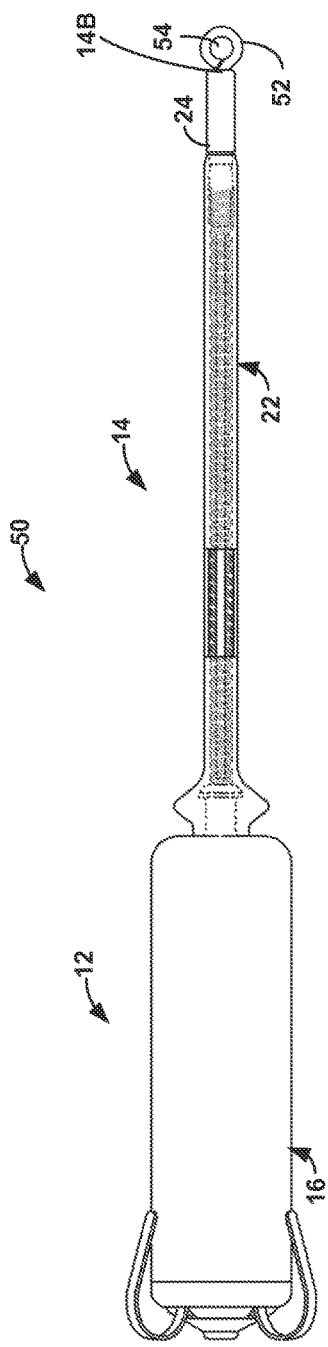
FIG. 5 illustrates another example leadless pacing system that comprises a leadless pacing device and a sensing extension.
Figure 6:
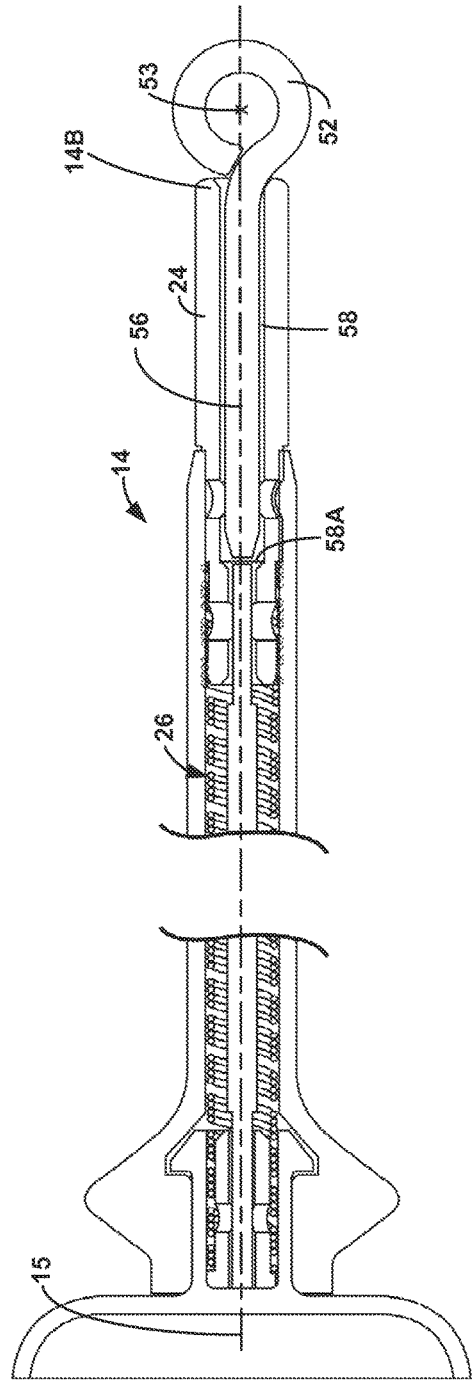
FIG. 6 is a schematic cross-sectional view of the sensing extension of FIG. 5.

Leadless pacing system 10 may be implanted in right ventricle 32, or another chamber of heart 34, using any suitable technique. In some cases, sensing extension 14 may include a feature that helps control a position of proximal end of sensing extension 14 during implantation of system 10 in patient 36. The feature may also be used to facilitate relatively easy capture of a proximal end of sensing extension 14 by a retrieval device, e.g., during explantation of system 10 from patient 36. FIGS. 5 and 6 illustrate an example of such a feature.

FIGS. 5 and 6 illustrate an example leadless pacing system 50, which is similar to system 10 of FIG. 1, but further includes eyelet 52 at a proximal end of sensing extension 14. In other examples of the system 50, however, the sensing extension may be any suitable extension, e.g., may not include a self-supporting body, as described above with respect to FIGS. 1 and 2, may include one or more additional electrodes, which may be used for sensing or electrical stimulation, or any combination thereof.

Eyelet 52 defines an opening 54 configured to receive, e.g., a tether or another tool used during implantation, during explanation, or both implantation and explanation. A tether may, for example, a suture thread or another material that is relatively thin and flexible, compared to sensing extension 14. The tether may be looped through opening 54 prior to inserting system 10 in right ventricle 32, and, after sensing extension 14 is implanted in heart 34 (FIG. 3), a clinician may pull back on the tether in order to pull back on proximal end 14B of sensing extension 14, to move proximal end 14B of sensing extension 14, or to otherwise control the position of proximal end 14B. In addition, eyelet 52 may be configured to facilitate capture of system 10 by a retrieval device, e.g. during explanation of system 10 from the patient or to move LPD 12 to another location after tines 18 have fixed to a particular location.

Although shown to have a circular cross-section in FIGS. 5 and 6, eyelet 52 may have any suitable cross-sectional shape configured to receive a tether or other tool. In addition, although shown in FIGS. 5 and 6 to define an opening that has a center axis 53 that is transverse and substantially orthogonal (e.g., orthogonal or nearly orthogonal) to longitudinal axis 15 of sensing extension 14, in other examples, center axis 53 may have another orientation relative to longitudinal axis 15. For example, the opening defined by eyelet 52 may be oriented such that center axis 53 is substantially parallel (e.g., parallel or nearly parallel) or oriented at an angle less than 90 degrees relative to to longitudinal axis 15. Thus, in some examples, the opening defined by eyelet 52 may be oriented such that center axis 53 is 90 degrees or less relative to longitudinal axis 15.

In addition, in some examples, center axis 53 may not be aligned with longitudinal axis 53, but, rather, eyelet 52 may extend away from a side surface of extension 14. In FIGS. 5 and 6, center axis 53 is aligned with longitudinal axis 53. However, if, for example, sensing extension 14 defines a curved proximal portion (e.g., as shown in FIGS. 4A-4C), center axis 53 may not be aligned with longitudinal axis 53.

Eyelet 52 may be mechanically connected to sensing extension 14 using any suitable technique. In the example shown in FIGS. 5 and 6, eyelet 52 includes base portion 56 that is received in cavity 58 defined by electrode 24. Electrode 24 and base portion 56 may be attached using any suitable technique, such as by crimping electrode 24 around base portion 56, via an adhesive, welding, or another suitable technique. The attachment between sensing extension 14 and eyelet 52 is strong enough to maintain the mechanical connection between eyelet 52 and sensing extension 14, even in the presence of forces (e.g., from a tether or other retrieval tool) pulling the eyelet 52 in a direction away from sensing extension 14. Likewise, the attachment between LPD 12 and sensing extension 14 is strong enough to maintain the mechanical connection between LPD 12 and sensing extension 14, even in the presence of forces pulling the sensing extension 14 and LPD 12 away from each other.

In some examples, end 58A of cavity 58 may be closed (i.e., cavity 58 may be a blind hole), which may help prevent environmental contaminants from being introduced into the portion of sensing extension 14 including conductor 26.

Eyelet 52 may be formed from any suitable material. In some examples, eyelet 52 is formed from an electrically nonconductive material. In other examples, eyelet 52 is formed from an electrically conductive material. In some examples in which eyelet 52 is formed from an electrically conductive material, eyelet 52 is configured to function as an extension of electrode 24. Thus, LPD 12 may sense electrical cardiac signals and deliver electrical stimulation with the aid of eyelet 52. Eyelet 52 may be electrically connected to electrode 24 by virtue of being in contact with electrode 24. In other examples in which eyelet 52 is formed from an electrically conductive material, the conductivity of eyelet 52 may be relatively low when compared to the conductive of electrode 24 for eyelet 52 to function as an extension of electrode 24. For example, eyelet 52 may be formed from stainless steel. In addition, eyelet 52 is configured to not be in contact with cardiac tissue when system 10 is implanted in a patient, e.g., sensing extension is configured to position eyelet not in contact with cardiac tissue, such that eyelet 52 may not function as a stimulation electrode.

Base portion 56 of eyelet 52 is shown in FIGS. 5 and 6 as being coaxial with a longitudinal axis of sensing extension 14, in some examples, base portion 56 may have another arrangement relative to the longitudinal axis of sensing extension 14. For example, in examples in which a proximal portion of extension 14 defines a curve (e.g., as shown in FIGS. 4A-4C), when eyelet 52 is positioned at a proximal end of sensing extension 14, base portion 56 may curve with the proximal portion. As another example, base portion 56 may be curvilinear or otherwise nonlinear (e.g., may define a 90 degree angle) and attached to sensing extension 14 such that base portion 56 extends away from electrode 24. Other configurations of eyelet 52 may also be used.

Eyelet 52 provides a feature for controlling a positioning of extension 52, as well as a feature that facilitates retrieval of system 50 from an implant site. These features may be useful with other type of extensions that are connected to electronics of LPD 12 (e.g., a stimulation module, a sensing module, or both). Thus, in some examples, system 50 may include an extension having a configuration different than sensing extension 14, the extension including eyelet 52 at a proximal end. For example, in FIGS. 5 and 6, rather than being connected to sensing extension 14 including electrode 24 electrically connected to conductive portion 16A of housing 16 of LPD 12, LPD 12 may be mechanically connected to an extension that includes multiple electrodes electrically connected to conductive portion 16A of housing 16, and the extension may extend away from housing 16 of LPD 12 and include eyelet 52 at a proximal end (similar to the position shown in FIG. 5).

As another example, LPD 12 may be mechanically connected to an extension that includes one or more electrodes that are not electrically connected to conductive portion 16A of housing 16, but, rather, connected to electronics (e.g., a sensing module and a stimulation module) of LPD 12 using another conductive path, such as a conductive feedthrough that extends through housing 16; in this example, eyelet 52 may be positioned at a proximal end of the extension, which may also extend away from housing 16. As yet another example, LPD 12 may be mechanically connected to an extension that is not self-supporting and/or includes one or more fixation elements. In these examples, eyelet 52 may be positioned at a proximal end of the extension. Other configurations of extensions including eyelet 52 are also contemplated.

Figure 7:
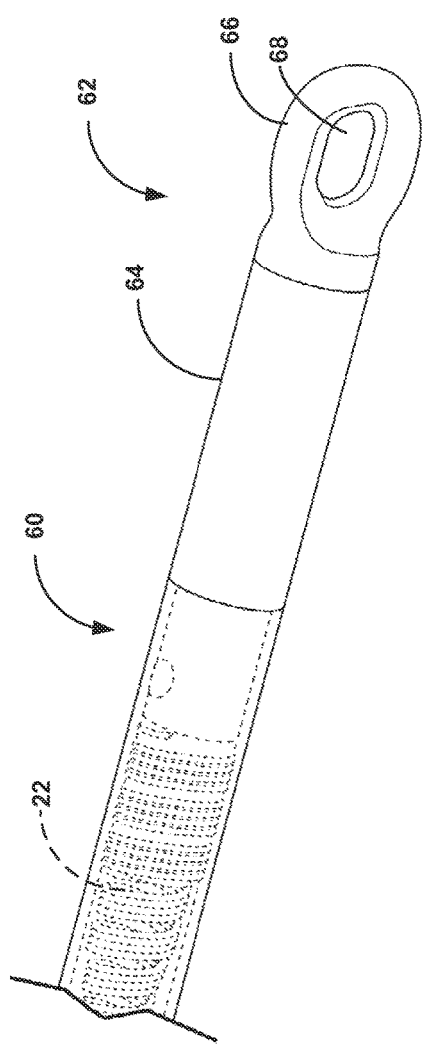
FIG. 7 is a perspective view of another example sensing extension.
Figure 8:
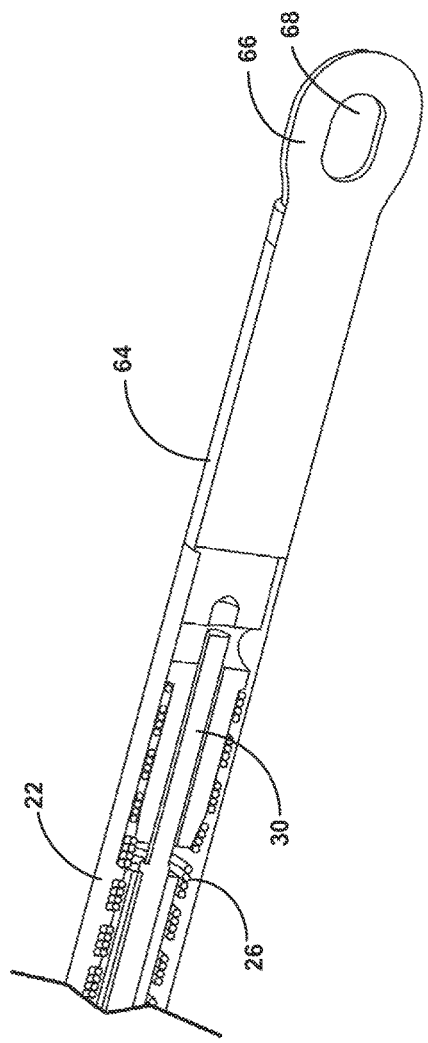
FIG. 8 is a cross-sectional perspective view of the sensing extension of FIG. 7.
Figure 9:
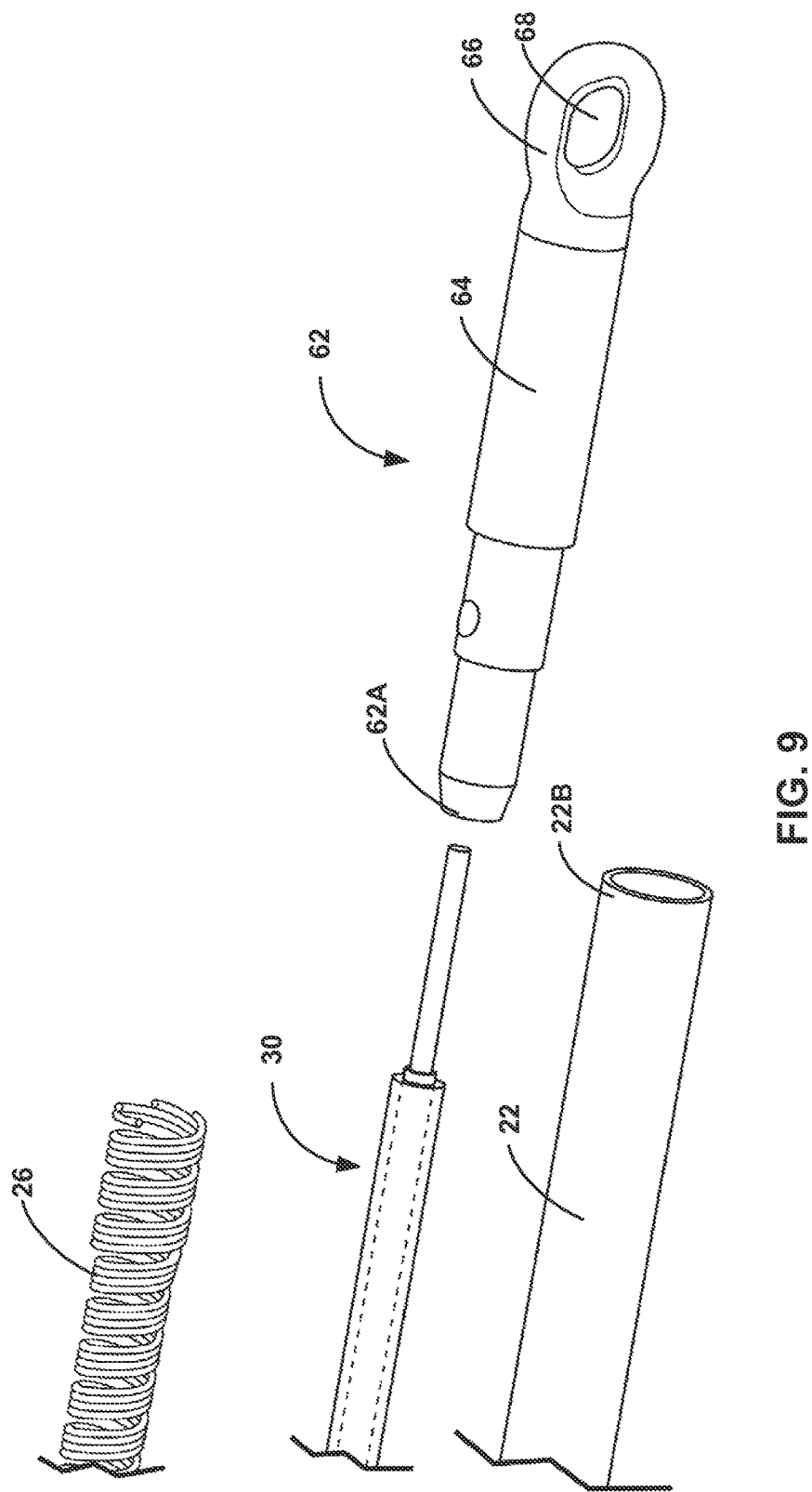
FIG. 9 is an exploded perspective view of the sensing extension of FIG. 7.

In other examples of system 50, sense electrode 24 and eyelet 52 may be integrated into a common, integral component. FIGS. 7-9 illustrate an example of such a sensing extension. FIG. 7 is a perspective view of example sensing extension 60, which may be similar to sensing extension 14 of FIGS. 5 and 6, but includes sense electrode 62 defining electrode portion 64 and eyelet portion 66 instead of sense electrode 24 and eyelet 52. FIG. 8 is a cross-sectional perspective view of sensing extension 60 and illustrates self-supporting body 22, electrical conductor 26, stiffness member 30, and sense electrode 62. FIG. 9 is an exploded perspective view of sensing extension 60.

As shown in FIGS. 7-9, electrode portion 64 and eyelet portion 66 are substantially continuous and are portions of a common body of sense electrode 62, rather than being separate components that are attached together. In contrast, sense electrode 24 and eyelet 52 shown in FIGS. 5 and 6 are separate components. Eyelet portion 66 is configured similarly to eyelet 52 and defines an opening 68 configured to receive, e.g., a tether or another tool used during implantation, during explanation, or both implantation and explanation.

Electrode 62 including integral electrode portion 64 and eyelet portion 66 may minimize the number of openings through which a fluid may enter an inner portion (e.g., where conductor 26 is positioned) of sensing extension 60.

Electrode 62 may be formed using any suitable technique. In some examples, electrode 62 may be produced with a cold-heading operation that defines a metal or other suitable electrically conductive material into the shape of electrode 62. In some examples, after forming the shape of electrode 62, eyelet portion 66 may be polished. All or only a part of electrode 62 may be electrically conductive. For example, in some examples, both electrode portion 64 and eyelet portion 66 are electrically conductive, though they may have different impedances, while in other examples, eyelet portion 66 is not electrically conductive and electrode portion 64 is electrically conductive. In some examples, to form electrode 62 including eyelet portion 66 that is not electrically conductive, eyelet portion 66 may be masked during the coating of electrode portion 62 with an electrically conductive material, such as titanium nitride (TiN).

As with electrode 24, sense electrode 62 may be electrically connected to electrical conductor 26, stiffness member 30, or both stiffness member 30 and electrical conductor 26 using any suitable technique, such as the ones described above with respect to electrode 24. For example, a proximal portion of conductor 26 or stiffness member 30 may be welded or crimped to a distal portion of electrode 62.

Electrode 62 may define a distal portion 62A that is configured to be received in self-supporting body 22. In addition, in some examples, as shown in FIG. 9, distal portion 62A may define an opening configured to receive stiffness member 30, such that stiffness member 30 and electrode 60 are partially co-extensive, e.g., overlap in a longitudinal direction. In other examples, however, stiffness member 30 and electrode 60 may not be co-extensive. Electrode 60 may, for example, provide sufficient stiffness to the proximal end of sensing extension 60 without stiffness member 30.

Electrode 62 may be mechanically connected to self-supporting body 22 using any suitable technique, such as by a friction fit achieved when distal portion 62A of electrode 62 is received in proximal end 22B of self-supporting body 22, by ultrasonic welding, by an adhesive, or any other suitable technique or combinations of techniques. The mechanical connection may define a relatively fluid tight seal between electrode 62 and self-supporting body 22 to help prevent the ingress of fluids into self-supporting body 22.

In each of the examples described herein, stiffness member 30 may comprise one or more elements. For example, in the example shown in FIG. 9, stiffness member 30 includes three members that are substantially co-axial. Using two or more elements to form stiffness member 30 may provide design freedom for achieving the desired stiffness of stiffness member 30 than, for example, one element.

Figure 10:
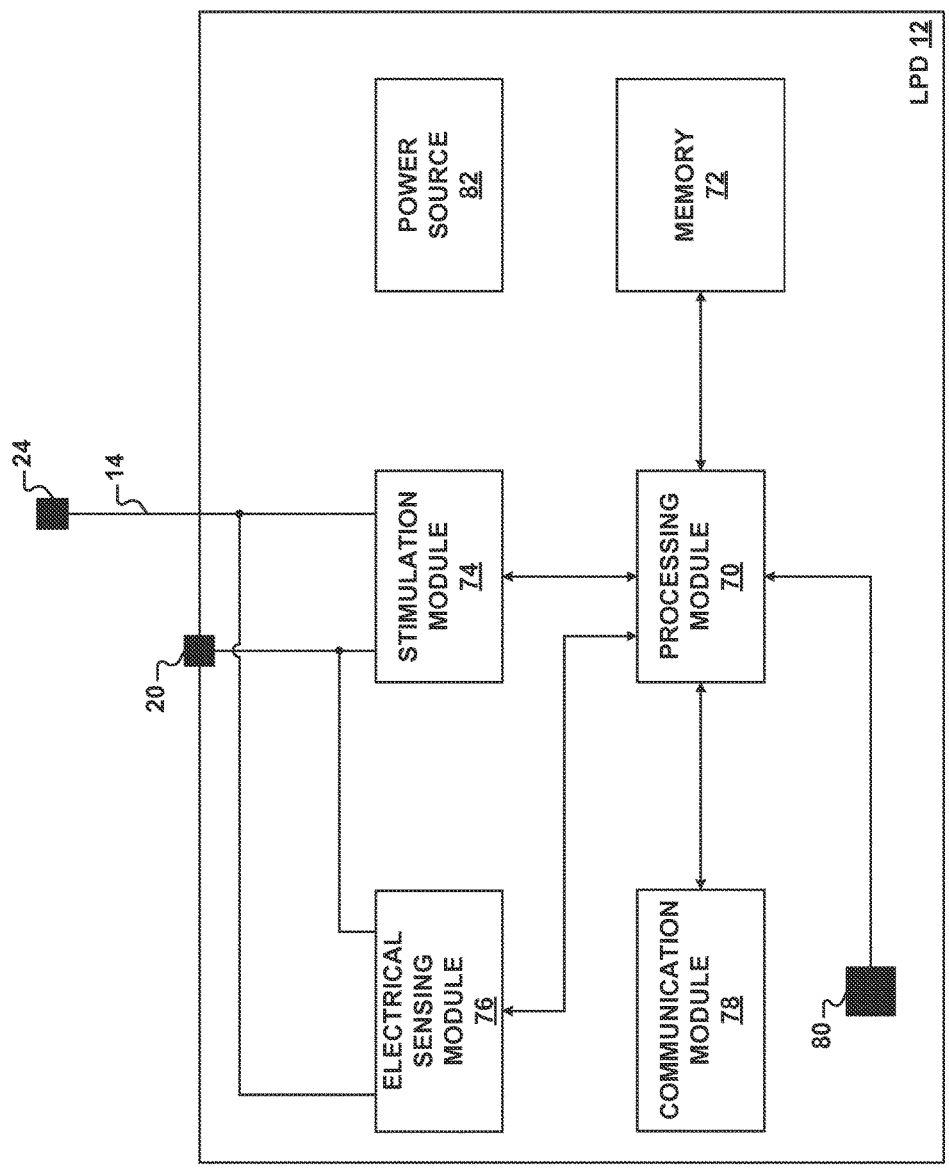
FIG. 10 is a functional block diagram of an example leadless pacing system.

FIG. 10 is a functional block diagram of an example LPD 12. LPD 12 includes a processing module 70, memory 72, stimulation module 74, electrical sensing module 76, communication module 78, sensor 80, and power source 82. Power source 82 may include a battery, e.g., a rechargeable or non-rechargeable battery.

Modules included in LPD 12 represent functionality that may be included in LPD 12 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 70 may include any one or more of a microprocessor, a controller, a digital signal processor (DSP), an application specific integrated circuit (ASIC), a field-programmable gate array (FPGA), or equivalent discrete or integrated logic circuitry. In some examples, processing module 70 may include multiple components, such as any combination of one or more microprocessors, one or more controllers, one or more DSPs, one or more ASICs, or one or more FPGAs, as well as other discrete or integrated logic circuitry.

Processing module 70 may communicate with memory 72. Memory 72 may include computer-readable instructions that, when executed by processing module 70, cause processing module 70 to perform the various functions attributed to processing module 70 herein. Memory 72 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory 72 may include instructions that, when executed by one or more processors, cause the modules to perform various functions attributed to the modules herein. For example, memory 72 may include pacing instructions and values. The pacing instructions and values may be updated by programmer 40 (FIG. 3).

Stimulation module 74 and electrical sensing module 76 are electrically coupled to electrodes 20, 24. Processing module 70 is configured to control stimulation module 74 to generate and deliver electrical stimulation to heart 34 (e.g., right ventricle 32 in the example shown in FIG. 3) via electrodes 20, 24. Electrical stimulation may include, for example, pacing pulses, or any other suitable electrical stimulation. Processing module 70 may control stimulation module 74 to deliver electrical stimulation therapy via electrodes 20, 24 according to one or more therapy programs including pacing instructions that define a ventricular pacing rate, which may be stored in memory 72.

In addition, processing module 70 is configured to control electrical sensing module 76 monitor signals from electrodes 20, 24 in order to monitor electrical activity of heart 34. Electrical sensing module 76 may include circuits that acquire electrical signals. Electrical signals acquired by electrical sensing module 76 may include intrinsic cardiac electrical activity, such as intrinsic atrial depolarization and/or intrinsic ventricular depolarization. Electrical sensing module 76 may filter, amplify, and digitize the acquired electrical signals to generate raw digital data. Processing module 70 may receive the digitized data generated by electrical sensing module 76. In some examples, processing module 70 may perform various digital signal processing operations on the raw data, such as digital filtering.

Processing module 70 may sense cardiac events based on the data received from electrical sensing module 76. For example, processing module 70 may sense atrial electrical activity based on the data received from electrical sensing module 76. For example, in examples in which LPD 12 and sensing extension 14 are implanted in right ventricle 32, processing module 70 may detect far field P-waves indicative of atrial activation events based on the data received from electrical sensing module 76. In some examples, processing module 70 may also sense ventricular electrical activity based on the data received from electrical sensing module 76. For example, processing module 70 may detect R-waves indicative of ventricular activation events based on the data received from electrical sensing module 76. In examples in which processor 70 uses both electrodes 20 and 24 for both R-wave and P-wave sensing, processor 70 may detect the R-waves and P-waves from the same sensed signal, and the sensing vector can be between electrodes 20, 24.

In some examples, in addition to electrical sensing module 76, LPD 12 includes sensor 80, which may comprise at least one of a variety of different sensors. For example, sensor 80 may comprise at least one of a pressure sensor and an accelerometer. Sensor 80 may generate signals that indicate at least one of parameter of patient 12, such as, but not limited to, at least one of: an activity level of patient 36, a hemodynamic pressure, and heart sounds.

Communication module 78 may include any suitable hardware (e.g., an antenna), firmware, software, or any combination thereof for communicating with another device, such as programmer 40 (FIG. 3) or a patient monitor. Under the control of processing module 70, communication module 78 may receive downlink telemetry from and send uplink telemetry to other devices, such as programmer 40 or a patient monitor, with the aid of an antenna included in communication module 78.

Figure 11:
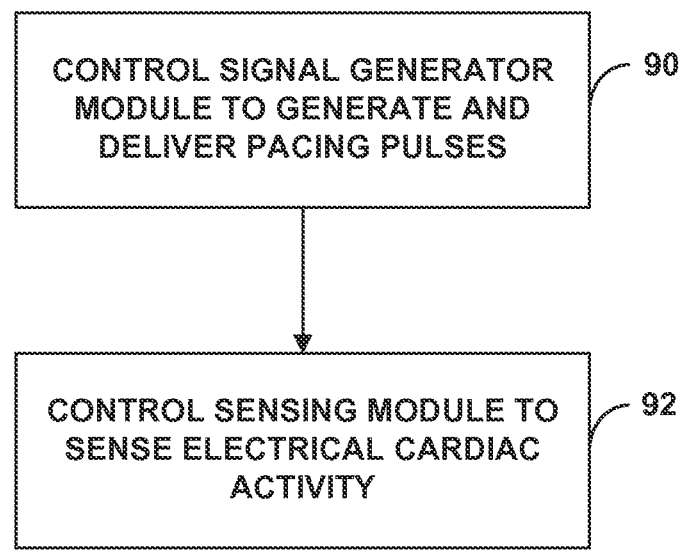
FIG. 11 is a flow diagram of an example technique for delivering therapy and sensing electrical cardiac activity with the leadless pacing system of FIG. 1.

FIG. 11 is a flow diagram of an example technique performed by leadless pacing system 10. While FIG. 11 is described as primarily being performed by processing module 70 of LPD 12, in other examples, another processor (e.g., a processor of programmer 40), alone or with the aid of processing module 70, may perform any part of the technique shown in FIG. 11. In addition, while the technique is described with reference to an example in which LPD 12 is implanted in right ventricle 32 (FIG. 3), the technique shown in FIG. 11 may also be used with other examples.

In accordance with the example shown in FIG. 11, processing module 70 controls stimulation module 74 to generate and deliver pacing pulses to right ventricle 32 via electrodes 20, 24 (90). For example, electrode 20 may be selected as a source electrode and electrode 24 may be selected as the sink electrode. Processing module 70 also controls electrical sensing module 76 (FIG. 10) to sense electrical cardiac activity with electrodes 20, 24 (92). The electrical cardiac activity can be, for example, any combination of the following: intrinsic ventricular depolarization, intrinsic atrial depolarization, other ventricular activation events (e.g., paced events), or other atrial activation events (e.g., paced events). Processing module 70 may receive sensed electrical cardiac signals from sensing module 76 and detect atrial depolarization by at least detecting a far field P-wave. In some examples, processing module 70 controls electrical sensing module 76 (FIG. 10) to sense electrical cardiac activity with electrodes 20, 24 during a refractory period of heart 34.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A system comprising:
    a leadless pacing device comprising:
        a stimulation module configured to generate pacing pulses;
        a sensing module;
        a processing module;
        a housing configured to be implanted within a chamber of a heart of a patient, wherein the housing encloses the stimulation module, the sensing module, and the processing module; and
        a first electrode electrically coupled to the sensing module and the stimulation module; and
    an extension extending from the housing and comprising:
        a body mechanically connected to the housing and comprising a conductor electrically connected to at least one of the sensing module or the stimulation module;
        a second electrode carried by the body and electrically connected to the conductor; and
        an eyelet at a proximal end of the extension, the eyelet defining an opening configured to receive a tether, wherein the opening defines a center axis that is not aligned with a longitudinal axis of the extension.

2. The system of claim 1, wherein the center axis is oriented 90 degrees or less relative to the longitudinal axis of the extension.

3. The system of claim 1, wherein the center axis is substantially parallel to a longitudinal axis of the extension.

4. The system of claim 1, wherein the housing comprises a conductive portion, and the conductor is electrically connected to the conductive portion, wherein the processing module is configured to control the sensing module to sense electrical cardiac activity via the second electrode.

5. The system of claim 1, wherein the body is a self-supporting body.

6. The system of claim 1, wherein the body is a self-supporting body comprising a curved proximal portion.

7. The system of claim 1, wherein the second electrode defines a blind hole configured to receive the eyelet.

8. The system of claim 1, wherein the second electrode and the eyelet are portions of a common body.

9. A method comprising:
    controlling, by a processor, a stimulation module of a leadless pacing device to deliver a pacing pulse to a patient, the leadless pacing device comprising:
        the stimulation module;
        a sensing module;
        the processor;
        a housing configured to be implanted within a chamber of a heart of a patient, wherein the housing encloses the stimulation module, the sensing module, and the processor; and
        a first electrode electrically coupled to the sensing module and the stimulation module; and
    controlling, by the processor, the sensing module of the leadless pacing device to sense electrical cardiac activity via the first electrode and a second electrode of an extension that extends from the housing, the extension further comprising:
        a body mechanically connected to the housing and comprising a conductor electrically connected to the sensing module, wherein the second electrode is carried by the body and is electrically connected to the conductor; and
        an eyelet at a proximal end of the extension, the eyelet defining an opening configured to receive a tether, wherein the opening defines a center axis that is not aligned with a longitudinal axis of the extension.

10. The method of claim 9, wherein the center axis is oriented 90 degrees or less relative to the longitudinal axis of the extension.

11. The method of claim 9, wherein the center axis is substantially parallel to a longitudinal axis of the extension.

12. The method of claim 9, wherein the body is a self-supporting body.

13. The method of claim 9, wherein the second electrode defines a blind hole configured to receive the eyelet.

14. The method of claim 9, wherein the second electrode and the eyelet are portions of a common body.

* * * * *